US010450606B2

(12) United States Patent
Bielas

(10) Patent No.: US 10,450,606 B2
(45) Date of Patent: Oct. 22, 2019

(54) COMPOSITIONS AND METHODS FOR ACCURATELY IDENTIFYING MUTATIONS

(71) Applicant: Fred Hutchinson Cancer Research Center, Seattle, WA (US)

(72) Inventor: Jason H. Bielas, Seattle, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 411 days.

(21) Appl. No.: 15/199,784

(22) Filed: Jun. 30, 2016

(65) Prior Publication Data

US 2016/0326578 A1 Nov. 10, 2016

Related U.S. Application Data

(62) Division of application No. 14/378,870, filed as application No. PCT/US2013/026505 on Feb. 15, 2013, now Pat. No. 10,011,871.

(60) Provisional application No. 61/600,535, filed on Feb. 17, 2012.

(51) Int. Cl.
| | |
|---|---|
| *C12Q 1/6874* | (2018.01) |
| *C12Q 1/6869* | (2018.01) |
| *C12N 15/10* | (2006.01) |
| *C12N 15/70* | (2006.01) |
| *C12N 15/81* | (2006.01) |
| *C12N 15/85* | (2006.01) |
| *C40B 40/08* | (2006.01) |
| *C40B 50/06* | (2006.01) |
| *C12Q 1/6827* | (2018.01) |

(52) U.S. Cl.
CPC ........... *C12Q 1/6874* (2013.01); *C12N 15/10* (2013.01); *C12N 15/1065* (2013.01); *C12N 15/1093* (2013.01); *C12N 15/70* (2013.01); *C12N 15/81* (2013.01); *C12N 15/85* (2013.01); *C12Q 1/6827* (2013.01); *C12Q 1/6869* (2013.01); *C40B 40/08* (2013.01); *C40B 50/06* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 5,308,751 A | 5/1994 | Ohkawa et al. | |
| 6,013,445 A | 1/2000 | Albrecht et al. | |
| 6,143,496 A | 11/2000 | Brown et al. | |
| 6,404,907 B1 | 6/2002 | Gilchrist et al. | |
| 6,818,395 B1 | 11/2004 | Quake et al. | |
| 6,833,246 B2 | 12/2004 | Balasubramanian | |
| 7,169,560 B2 | 1/2007 | Lapidus et al. | |
| 7,264,929 B2 | 9/2007 | Rothberg et al. | |
| 7,282,337 B1 | 10/2007 | Harris et al. | |
| 7,537,897 B2 | 5/2009 | Brenner et al. | |
| 7,666,593 B2 | 2/2010 | Lapidus | |
| 7,700,286 B2 | 4/2010 | Stroun et al. | |
| 7,754,429 B2 | 7/2010 | Rigatti et al. | |
| 8,168,385 B2 | 5/2012 | Brenner | |
| 8,318,434 B2 | 11/2012 | Cuppens | |
| 8,383,345 B2 | 2/2013 | Shendure et al. | |
| 8,586,310 B2 | 11/2013 | Mitra et al. | |
| 8,741,606 B2 | 6/2014 | Casbon et al. | |
| 8,865,410 B2 | 10/2014 | Shendure et al. | |
| 9,085,798 B2 | 7/2015 | Chee | |
| 9,404,156 B2 | 8/2016 | Hicks et al. | |
| 9,476,095 B2 | 10/2016 | Vogelstein et al. | |
| 9,752,188 B2 | 9/2017 | Schmitt et al. | |
| 10,011,871 B2 | 7/2018 | Bielas | |
| 2002/0164629 A1 | 11/2002 | Quake et al. | |
| 2005/0019776 A1 | 1/2005 | Callow et al. | |
| 2008/0261204 A1 | 10/2008 | Lexow | |
| 2009/0026082 A1 | 1/2009 | Rothberg et al. | |
| 2009/0099041 A1 | 4/2009 | Church et al. | |
| 2009/0127589 A1 | 5/2009 | Rothberg et al. | |
| 2009/0156412 A1 | 6/2009 | Harris et al. | |
| 2009/0191565 A1 | 7/2009 | Lapidus et al. | |
| 2009/0215633 A1 | 8/2009 | Van Eijk et al. | |
| 2010/0035252 A1 | 2/2010 | Rothberg et al. | |
| 2010/0137143 A1 | 6/2010 | Rothberg et al. | |
| 2010/0188073 A1 | 7/2010 | Rothberg et al. | |
| 2010/0197507 A1 | 8/2010 | Rothberg et al. | |
| 2010/0227329 A1 | 9/2010 | Cuppens | |

(Continued)

FOREIGN PATENT DOCUMENTS

| | | |
|---|---|---|
| DE | 10 2008 025 656 A1 | 12/2009 |
| DE | 102008025656 A1 | 12/2009 |

(Continued)

OTHER PUBLICATIONS

Kinde et al., "Detection and quantification of rare mutations with massively parallel sequencing," Proc. Natl. Acad. Sci. USA 2011, 108:9530-9535, with 10 pages of Supporting Information, published online May 17, 2011. (Year: 2011).*

(Continued)

*Primary Examiner* — Kaijiang Zhang

(74) *Attorney, Agent, or Firm* — Mintz, Levin, Cohn, Ferris, Glovsky and Popeo, P.C.

(57) ABSTRACT

The present disclosure provides compositions and methods for accurately detecting mutations by uniquely tagging double stranded nucleic acid molecules with dual cyphers such that sequence data obtained from a sense strand can be linked to sequence data obtained from an anti-sense strand when sequenced, for example, by massively parallel sequencing methods.

25 Claims, 6 Drawing Sheets

Specification includes a Sequence Listing.

(56) References Cited

U.S. PATENT DOCUMENTS

| | | | |
|---|---|---|---|
| 2010/0282617 | A1 | 11/2010 | Rothberg et al. |
| 2010/0300559 | A1 | 12/2010 | Schultz et al. |
| 2010/0300895 | A1 | 12/2010 | Nobile et al. |
| 2010/0301398 | A1 | 12/2010 | Rothberg et al. |
| 2010/0304982 | A1 | 12/2010 | Hinz et al. |
| 2012/0058468 | A1 | 3/2012 | McKeown |
| 2012/0283110 | A1 | 11/2012 | Shendure et al. |
| 2013/0005585 | A1 | 1/2013 | Anderson et al. |
| 2014/0155274 | A1 | 6/2014 | Xie et al. |
| 2015/0044687 | A1 | 2/2015 | Schmitt et al. |
| 2015/0087535 | A1 | 3/2015 | Patel |
| 2018/0363048 | A1 | 12/2018 | Bielas |
| 2018/0363049 | A1 | 12/2018 | Bielas |

FOREIGN PATENT DOCUMENTS

| | | | |
|---|---|---|---|
| EP | 2828218 A1 | 1/2015 | |
| JP | 4747245 B2 | 8/2011 | |
| WO | 96/12039 A1 | 4/1996 | |
| WO | 98/44151 A1 | 10/1998 | |
| WO | 00/18957 A1 | 4/2000 | |
| WO | 00/60124 A2 | 10/2000 | |
| WO | 2004/003136 A2 | 1/2004 | |
| WO | 2005/042759 A2 | 5/2005 | |
| WO | 2005/068656 A1 | 7/2005 | |
| WO | WO-2005/063980 A1 | 7/2005 | |
| WO | 2006/084130 A2 | 8/2006 | |
| WO | WO-2006/137733 A1 | 12/2006 | |
| WO | WO-2007/037678 A2 | 4/2007 | |
| WO | WO-2007/037678 A3 | 4/2007 | |
| WO | 2007/073171 A2 | 6/2007 | |
| WO | WO-2007/073165 A1 | 6/2007 | |
| WO | 2007/106509 A2 | 9/2007 | |
| WO | WO-2007/114693 A2 | 10/2007 | |
| WO | WO-2007/114693 A3 | 10/2007 | |
| WO | 2009/036525 A2 | 3/2009 | |
| WO | 2009/152928 A2 | 12/2009 | |
| WO | 2010/115100 A1 | 10/2010 | |
| WO | 2010/115154 A1 | 10/2010 | |
| WO | WO-2010/126614 A2 | 11/2010 | |
| WO | WO-2010/126614 A3 | 11/2010 | |
| WO | WO-2011/155833 A2 | 12/2011 | |
| WO | WO-2011/155833 A3 | 12/2011 | |
| WO | WO-2012/038839 A2 | 3/2012 | |
| WO | WO-2012/038839 A3 | 3/2012 | |
| WO | 2012/106546 A2 | 8/2012 | |
| WO | WO-2012/142213 A2 | 10/2012 | |
| WO | WO-2012/142213 A3 | 10/2012 | |
| WO | 2012/148477 A1 | 11/2012 | |
| WO | 2013/123442 A1 | 8/2013 | |
| WO | WO-2013/142389 A1 | 9/2013 | |
| WO | WO-2013/181170 A1 | 12/2013 | |

OTHER PUBLICATIONS

Casbon, J.A. et al. (Jul. 2011, e-published Apr. 13, 2011). "A method for counting PCR template molecules with application to next-generation sequencing," Nuclec Acids Res 39(12):e81.

Extended European Search Report dated Jun. 13, 2018, for EP Application No. 18150361.6, 6 pages.

Kou, et al., "Benefits and Challenges with Applying Unique Molecular Identifiers in Next Generation Sequencing to Detect Low Frequency Mutations", PLoS One, 11(1):e0146638, 2016.

Travers, et al., "A flexible and efficient template format for circular consensus sequencing and SNP detection", NAR, 38 (15), Aug. 1, 2010, 1-8.

Jabara et al., "Accurate sampling and deep sequencing of the HIV-1 protease gene using a Primer ID", Proc Natl Acad Sci U S A, 108(50):20166-20171 (2011).

Bielas et al., "Human cancers express a mutator phenotype," Proc. Natl. Acad. Sci. USA 103(48):18238-18242 (2006).

Bielas et al., "Quantification of random genomic mutations," Nat. Methods 2(4):285-290 (2005).

Bowtell, "The genesis and evolution of high-grade serous ovarian cancer," Nat. Rev. Cancer 10(11):803-808 (2010).

Brandon et al., "Mitochondrial mutations in cancer," Oncogene 25(34):4647-4662 (2006).

Cancer Genome Atlas Research Network, "Integrated Genomic Analyses of Ovarian Carcinoma," Nature 474(7353):609-615 (2011).

Chatterjee et al., "Mitochondrial DNA mutations in human cancer," Oncogene 25(34):4663-4674 (2006).

Copeland et al., "Mitochondrial DNA Alterations in Cancer," Cancer Invest. 20(4):557-569 (2002).

Hug et al., "Measurement of the Number of Molecules of a Single mRNA Species in a Complex mRNA Preparation," J. theor. Biol. 221(4):615-624 (2003).

Jones et al., "Comparative lesion sequencing provides insights into tumor evolution," Proc. Natl. Acad. Sci. USA 105(11):4283-4288 (2008).

Kinde et al. "Detection and quantification of rare mutations with massively parallel sequencing," Proc. Natl. Acad. Sci. USA 108(23):9530-9535 (2011).

Kraytsberg et al., "Single molecule PCR in mtDNA mutational analysis: genuine mutations vs. damage bypass-derived artifacts," Methods 46(4):269-273 (2008).

McCloskey et al., "Encoding PCR Products with Batch-stamps and Barcodes," Biochem. Genet. 45:761-767 (2007).

Niedringhaus et al., "Landscape of Next-Generation Sequencing Technologies," Anal. Chem. 83(12):4327-4341 (2011).

Taylor et al., "Mitochondrial DNA mutations in human disease," Nat. Rev. Genet. 6(5):389-402 (2005).

Zheng et al., "Origins of human mitochondrial point mutations as DNA polymerase y-mediated errors," Mutat. Res. 599(1-2):11-20 (2006).

Bainbridge, et al., "Whole exome capture in solution with 3 Gbp of data", Genome Biology 11: R62, 2010.

Baird, et al., "Rapid SNP Discovery and Genetic Mapping Using Sequenced RAD markers", PLOS One, 3(10):e3376, 2008, 1-7.

Brockman, et al., "Quality scores and SNP detection in sequencing-by-synthesis systems", Methods, 18, 2008, 763-770.

Chmielecki, et al., "Targeted next-generation sequencing of DNA regions proximal to a conserved GXGXXG signaling motif enables systematic discovery of tyrosine kinase fusions in cancer", Nucleic Acids Research, vol. 38, No. 20, 2010, 6985-6996.

Fleishmann, et al., "Whole-genome random sequencing and assembly of Haemophilus influenzae Rd", Science, vol. 269, issue 5223, 1995, 496-512.

Fullwood, et al., "Next-generation DNA sequencing of paired-end tags (PET) for transcriptome and genome analyses", Genome Res, 19, 2009, 521-532.

Hashimoto, et al., "5'-end SAGE for the analysis of transcriptional start sites", Nature Biotechnology, 22, 2004, 1146-1149.

Hiatt, et al., "Parallel, tag-directed assembly of locally derived short sequence reads", Nature Methods, 7(2), 2010, 119-122.

Homer, et al., "Improved variant discovery through local re-alignment of short-read next-generation sequencing data using SRMA", Genome Biology, 11:R99, 2010.

Huse, et al., "Accuracy and quality of massively parallel DNA pyrosequencing", Genome Biology, 8:RI43, 2007.

Kivioja, et al., "Counting absolute numbers of molecules using unique molecular identifiers", Nat Methods, 9(1), 2011, 72-4.

Korbel, et al., "Paired-End Mapping Reveals Extensive Structural Variation in the Human Genome", Science, 318(5849), 2007, 420-426.

Li, et al., "A new approach for detecting low-level mutations in next-generation sequence data", Genome Biology, 13:R34, 2012.

Linnarsson, "Recent advances in DNA sequencing methods—general principles of sample preparaton", Experimental Cell Research, 316, 2010, 1339-1343.

Metzker, "Sequencing technologies—the next generation", Nature Reviews Genetics, 11, 2010, 31-46.

Ng, et al., "Gene identification signature (GIS) analysis for transcriptome characterization and genome annotation", Nature Methods, 2(2), 2005, 105-111.

(56) References Cited

OTHER PUBLICATIONS

Ng, et al., "Multiplex sequencing of paired-end ditags (MS-PET): a strategy for the ultra-high-throughput analysis of transcriptomes and genomes", NAR, 34(12), 2006, e84.
Saha, et al., "Using the transcriptome to annotate the genome", Nature Biotechnology, 20, 2002, 508-512.
Schmitt, et al., "Detection of ultra-rare mutations by next-generation sequencing", PNAS, vol. 109, No. 36, 2012, 14508-14513.
Shiroguchi, et al., "Digital RNA Sequencing Minimizes Sequence-dependent Bias and Amplification Noise with Optimized Single-molecule Barcodes", PNAS 109(4), 2012, 1347-1352.
Srivatsan, et al., "High-Precision, Whole-Genome Sequencing of Laboratory Strains Facilitates Genetic Studies", PLoS Genet, 4(8) el000139, 2008.
Varley, et al., "Bisulfite Patch PCR enables multiplexed sequencing of promoter methylation across cancer samples", Genome Research, 20, 2010, 1279-87.
Velculescu, et al., "Serial analysis of gene expression", Science, vol. 270, No. 5235, 1995, 484-487.
Walsh, et al., "Detection of inherited mutations for breast and ovarian cancer using genomic capture and massively parallel sequencing", PNAS, vol. 107, No. 28, 2010, 12629-12633.
Wei, et al., "5' Long serial analysis of gene expression (LongSAGE) and 3' LongSAGE for transcriptome characterization and genome annotation", PNAS, vol. 101, No. 32, 2004, 11701-11706.
Zhang, et al., "The impact of next-generation sequencing on genomics", J Genet Genomics, 38(3), 2011, 95-109.
Zilberman, et al., "Genome-wide analysis of DNA methylation patterns", Development, 134, 2007, 3959-3965.
McCloskey et al., Encoding PCR Products with Batch-stamps and Barcodes,: Biochem Genet., 45(11-12):761-767 (2007).
Bielas et al., "Quantification of Random Genomic Mutations," Nature Methods 2(4):285-290 (2005).
Chaterjee et al., "Mitchondrial DNA Mutations in Human Cancer," Oncogene 25(34):4663-4674 (2006).
Zheng et al, "Origins of Human Mitochondrial Point Mutations as DNA Polymerase γ-mediated Errors," Mutat. Res. 599(1-2):11-20 (2006).
Bettegowda, et al., "Detection of circulating tumor DNA in early- and late-stage human malignancies", SciTrans Med, vol. 6. No. 224, 2014, 1-11.
Braslavsky, et al., "Sequence information can be obtained from single DNA molecules", PNAS, vol. 100, No. 7, 2003, 3960-3964.
Duncavage, et al., "Hybrid Capture and Next-Generation Sequencing Identify Viral Integration Sites from Formalin-Fixed, Paraffin-Embedded Tissue", J Mol Diagn., vol. 13, No. 3, 2011, 325-333.
Harris, et al., "Single-Molecule DNA Sequencing of a Viral Genome", Science, vol. 320, 2008, 106-109.
Mardis, et al., "The impact of next-generation sequencing technology on genetics", Trends Genet 24(2), 2008, 133-141.
Marguiles, et al., "Genome sequencing in microfabricated high-density picolitre reactors", Nature 437(7057), 2005, 376-380.
Maxam, et al., "A new method for sequencing DNA", PNAS, vol. 74, No. 2, 1997, 560-564.
Moudrianakis, et al., "Base Sequence Determination In Nucleic Acids With The Electron Microscope III. chemistry and microscopy of guanine-labeled DNA", PNAS, vol. 53, No. 3, 1965, 564-671.
Mouliere, et al., "Circulating tumor-derived DNA is shorter than somatic DNA in plasma", PNAS, vol. 112, No. 11, 2015, 3178-3179.
Mouliere, et al., "Multi-marker Analysis of Circulating Cell-free DNA Toward Personalized Medicine for Colorectal Cancer", Mol Oncol., vol. 8, No. 5, Mar. 2014, 927-947.
Newman, et al., "An ultrasensitive method for quantitating circulating tumor DNA with broad patient coverage", Nat Med, vol. 20, No. 5, 2014, 548-554.
Sanger, et al., "DNA sequencing with chain-terminating inhibitors", PNAS, vol. 74, No. 12, 1997, 5463-5467.
Soni, et al., "Progress toward ultrafast DNA sequencing using solid-state nanopores", Clin. Chem, 53(11), 2007, 1996-2001.
Notice of Opposition to European Patent 2,814,959 and Arguments in Support of Same (dated Oct. 2018), 21 pages.
European Third Party Observations dated Mar. 18, 2019, for EP Application No. 18 150 361.6, 22 pages.
European Examination Report dated Apr. 12, 2019, for EP Application No. 18 150 361.6, 4 pages.
European Summons to Attend Oral Proceedings Pursuant to Rule 115(1) EPC, and Provisional Opinion dated Aug. 6, 2019, for EP Patent Application No. 13706397.0, 10 pages.

\* cited by examiner

COMPOSITIONS AND METHODS FOR ACCURATELY IDENTIFYING MUTATIONS

CROSS REFERENCE TO RELATED APPLICATION

This application is a divisional of U.S. patent application Ser. No. 14/378,870, filed Aug. 14, 2014, which is a U.S. National Stage Application under 35 U.S.C. § 371 of International Patent Application No. PCT/US2013/026505, filed Feb. 15, 2013, which claims the benefit of U.S. provisional patent application Ser. No. 61/600,535, filed Feb. 17, 2012, which are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 14303-004-999_SEQ_LIST.txt. The text file is 2,490 bytes, was created on Jul. 29, 2016, and is being submitted electronically via EFS-Web.

BACKGROUND

1. Technical Field

The present disclosure relates to compositions and methods for accurately detecting mutations using sequencing and, more particularly, uniquely tagging double stranded nucleic acid molecules such that sequence data obtained for a sense strand can be linked to sequence data obtained from the anti-sense strand when obtained via massively parallel sequencing methods.

2. Description of Related Art

Detection of spontaneous mutations (e.g., substitutions, insertions, deletions, duplications), or even induced mutations, that occur randomly throughout a genome can be challenging because these mutational events are rare and may exist in one or only a few copies of DNA. The most direct way to detect mutations is by sequencing, but the available sequencing methods are not sensitive enough to detect rare mutations. For example, mutations that arise de novo in mitochondrial DNA (mtDNA) will generally only be present in a single copy of mtDNA, which means these mutations are not easily found since a mutation must be present in as much as 10-25% of a population of molecules to be detected by sequencing (Jones et al., *Proc. Nat'l. Acad. Sci. U.S.A.* 105:4283-88, 2008). As another example, the spontaneous somatic mutation frequency in genomic DNA has been estimated to be as low as $1\times10^{-8}$ and $2.1\times10^{-6}$ in human normal and cancerous tissues, respectively (Bielas et al., *Proc. Nat'l Acad. Sci. U.S.A.* 103:18238-42, 2008).

One improvement in sequencing has been to take individual DNA molecules and amplify the number of each molecule by, for example, polymerase chain reaction (PCR) and digital PCR. Indeed, massively parallel sequencing represents a particularly powerful form of digital PCR because multiple millions of template DNA molecules can be analyzed one by one. However, the amplification of single DNA molecules prior to or during sequencing by PCR and/or bridge amplification suffers from the inherent error rate of polymerases employed for amplification, and spurious mutations generated during amplification may be misidentified as spontaneous mutations from the original (endogenous unamplified) nucleic acid. Similarly, DNA templates damaged during preparation (ex vivo) may be amplified and incorrectly scored as mutations by massively parallel sequencing techniques. Again, using mtDNA as an example, experimentally determined mutation frequencies are strongly dependent on the accuracy of the particular assay being used (Kraytsberg et al., *Methods* 46:269-73, 2008)—these discrepancies suggest that the spontaneous mutation frequency of mtDNA is either below, or very close to, the detection limit of these technologies. Massively parallel sequencing cannot generally be used to detect rare variants because of the high error rate associated with the sequencing process—one process using bridge amplification and sequencing by synthesis has shown an error rate that varies from about 0.06% to 1%, which depends on various factors including read length, base-calling algorithms, and the type of variants detected (see Kinde et al., *Proc. Nat'l. Acad. Sci. U.S.A.* 108:9530-5, 2011).

BRIEF SUMMARY

In one aspect, the present disclosure provides a double-stranded nucleic acid molecule library that includes a plurality of target nucleic acid molecules and a plurality of random cyphers, wherein the nucleic acid library comprises molecules having a formula of $X^a$—$X^b$—Y, $X^b$—$X^a$—Y, Y—$X^a$—$X^b$, Y—$X^b$—$X^a$, $X^a$—Y—$X^b$, or $X^b$—Y—$X^a$ (in 5' to 3' order), wherein (a) $X^a$ comprises a first random cypher, (b) Y comprises a target nucleic acid molecule, and (c) $X^b$ comprises a second random cypher. Furthermore, each of the plurality of random cyphers comprise a length ranging from about 5 nucleotides to about 50 nucleotides (or about 5 nucleotides to about 10 nucleotides, or a length of about 6, about 7, about 8, about 9, about 10, about 11, about 12, about 13, about 14, about 15, about 16, about 17, about 18, about 19, or about 20 nucleotides).

In certain embodiments, the double-stranded sequences of the $X^a$ and $X^b$ cyphers are the same (e.g., $X^a$=$X^b$) for one or more target nucleic acid molecules, provided that each such target nucleic acid molecule does not have the same double-stranded cypher sequence as any other such target nucleic acid molecule. In certain other embodiments, the double-stranded sequence of the $X^a$ cypher for each target nucleic acid molecule is different from the double-stranded sequence of the $X^b$ cypher. In further embodiments, the double-stranded nucleic acid library is contained in a self-replicating vector, such as a plasmid, cosmid, YAC, or viral vector.

In a further aspect, the present disclosure provides a method for obtaining a nucleic acid sequence or accurately detecting a true mutation in a nucleic acid molecule by amplifying each strand of the aforementioned double-stranded nucleic acid library wherein a plurality of target nucleic acid molecules and plurality of random cyphers are amplified, and sequencing each strand of the plurality of target nucleic acid molecules and plurality of random cyphers. In certain embodiments, the sequencing is performed using massively parallel sequencing methods. In certain embodiments, the sequence of one strand of a target nucleic acid molecule associated with the first random cypher aligned with the sequence of the complementary strand associated with the second random cypher results in a measureable sequencing error rate ranging from about $10^{-6}$ to about $10^{-8}$.

DETAILED DESCRIPTION

Figure 1:
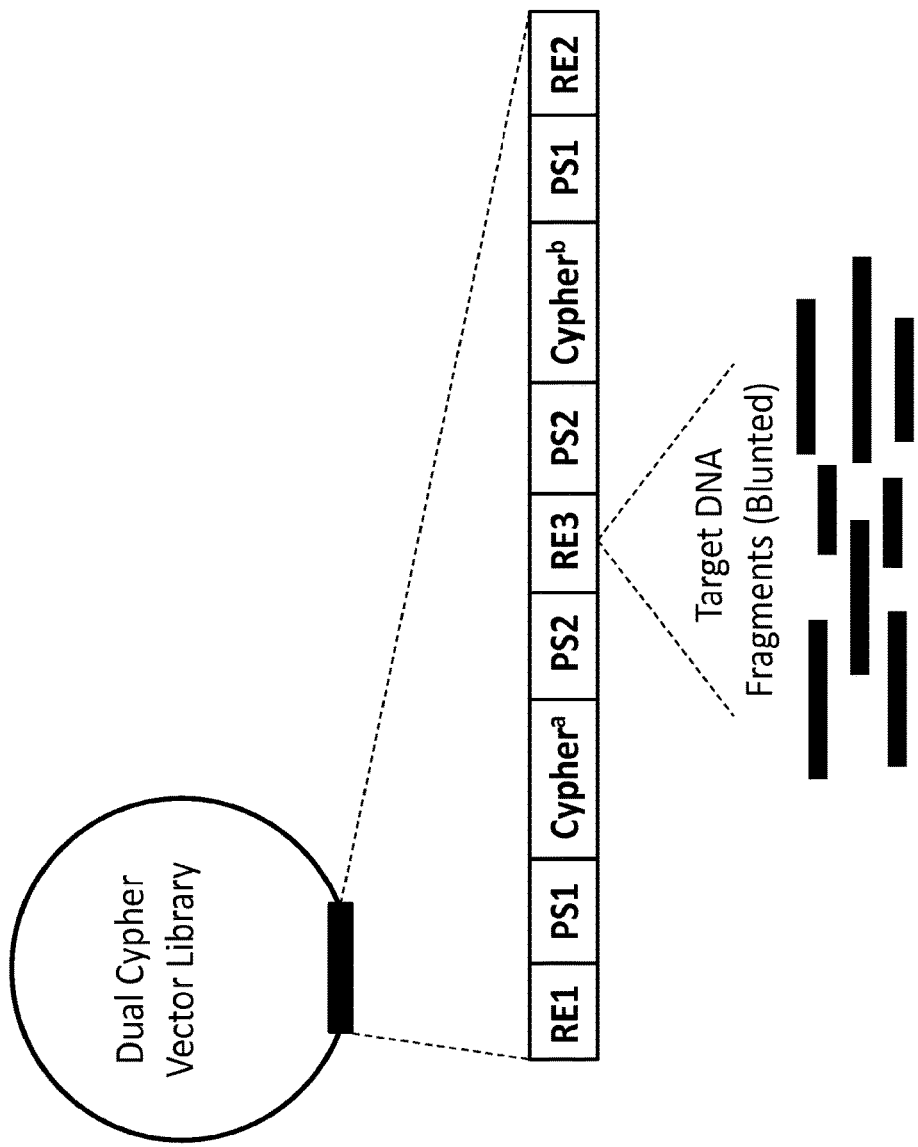
FIG. 1 is a cartoon illustration of an exemplary vector of the present disclosure useful for generating a double-stranded nucleic acid library.

In one aspect, the present disclosure provides a double-stranded nucleic acid library wherein target nucleic acid molecules include dual cyphers (i.e., barcodes or origin identifier tags), one on each end (same or different), so that sequencing each complementary strand can be connected or linked back to the original molecule. The unique cypher on each strand links each strand with its original complementary strand (e.g., before any amplification), so that each paired sequence serves as its own internal control. In other words, by uniquely tagging double-stranded nucleic acid molecules, sequence data obtained from one strand of a single nucleic acid molecule can be specifically linked to sequence data obtained from the complementary strand of that same double-stranded nucleic acid molecule. Furthermore, sequence data obtained from one end of a double-stranded target nucleic acid molecule can be specifically linked to sequence data obtained from the opposite end of that same double-stranded target nucleic acid molecule (if, for example, it is not possible to obtain sequence data across the entire target nucleic acid molecule fragment of the library).

The compositions and methods of this disclosure allow a person of ordinary skill in the art to more accurately distinguish true mutations (i.e., naturally arising in vivo mutations) of a nucleic acid molecule from artifact "mutations" (i.e., ex vivo mutations or errors) of a nucleic acid molecule that may arise for various reasons, such as a downstream amplification error, a sequencing error, or physical or chemical damage. For example, if a mutation pre-existed in the original double-stranded nucleic acid molecule before isolation, amplification or sequencing, then a transition mutation of adenine (A) to guanine (G) identified on one strand will be complemented with a thymine (T) to cysteine (C) transition on the other strand. In contrast, artifact "mutations" that arise later on an individual (separate) DNA strand due to polymerase errors during isolation, amplification or sequencing are extremely unlikely to have a matched base change in the complementary strand. The approach of this disclosure provides compositions and methods for distinguishing systematic errors (e.g., polymerase read fidelity errors) and biological errors (e.g., chemical or other damage) from actual known or newly identified true mutations or single nucleotide polymorphisms (SNPs).

In certain embodiments, the two cyphers on each target molecule have sequences that are distinct from each other and, therefore, provide a unique pair of identifiers wherein one cypher identifies (or is associated with) a first end of a target nucleic acid molecule and the second cypher identifies (or is associated with) the other end of the target nucleic acid molecule. In certain other embodiments, the two cyphers on each target molecule have the same sequence and, therefore, provide a unique identifier for each strand of the target nucleic acid molecule. Each strand of the double-stranded nucleic acid library (e.g., genomic DNA, cDNA) can be amplified and sequenced using, for example, next generation sequencing technologies (such as, emulsion PCR or bridge amplification combined with pyrosequencing or sequencing by synthesis, or the like). The sequence information from each complementary strand of a first double-stranded nucleic acid molecule can be linked and compared (e.g., computationally "de-convoluted") due to the unique cyphers associated with each end or strand of that particular double-stranded nucleic acid molecule. In other words, each original double-stranded nucleic acid molecule fragment found in a library of molecules can be individually reconstructed due to the presence of an associated unique barcode or pair of barcode (identifier tag) sequences on each target fragment or strand.

By way of background, any spontaneous or induced mutation will be present in both strands of a native genomic, double-stranded DNA molecule. Hence, such a mutant DNA template amplified using PCR will result in a PCR product in which 100% of the molecules produced by PCR include the mutation. In contrast to an original, spontaneous mutation, a change due to polymerase error will only appear in one strand of the initial template DNA molecule (while the other strand will not have the artifact mutation). If all DNA strands in a PCR reaction are copied equally efficiently, then any polymerase error that emerges from the first PCR cycle likely will be found in at least 25% of the total PCR product. But DNA molecules or strands are not copied equally efficiently, so DNA sequences amplified from the strand that incorporated an erroneous nucleotide base during the initial amplification might constitute more or less than 25% of the population of amplified DNA sequences depending on the efficiency of amplification, but still far less than 100%. Similarly, any polymerase error that occurs in later PCR cycles will generally represent an even smaller proportion of PCR products (i.e., 12.5% for the second cycle, 6.25% for the third, etc.) containing a "mutation." PCR-induced mutations may be due to polymerase errors or due to the polymerase bypassing damaged nucleotides, thereby resulting in an error (see, e.g., Bielas and Loeb, *Nat. Methods* 2:285-90, 2005). For example, a common change to DNA is the deamination of cytosine, which is recognized by Taq polymerase as a uracil and results in a cytosine to thymine transition mutation (Zheng et al., *Mutat. Res.* 599:11-20, 2006)—that is, an alteration in the original DNA sequence may be detected when the damaged DNA is sequenced, but such a change may or may not be recognized as a sequencing reaction error or due to damage arising ex vivo (e.g., during or after nucleic acid isolation).

Due to potential artifacts and alterations of nucleic acid molecules arising from isolation, amplification and sequencing, the accurate identification of true somatic DNA mutations is difficult when sequencing amplified nucleic acid molecules. Consequently, evaluation of whether certain mutations are related to, or are a biomarker for, various disease states (e.g., cancer) or aging becomes confounded.

Next generation sequencing has opened the door to sequencing multiple copies of an amplified single nucleic acid molecule—referred to as deep sequencing. The thought on deep sequencing is that if a particular nucleotide of a nucleic acid molecule is sequenced multiple times, then one can more easily identify rare sequence variants or mutations. In fact, however, the amplification and sequencing process has an inherent error rate (which may vary depending on DNA quality, purity, concentration (e.g., cluster density), or other conditions), so no matter how few or how many times a nucleic acid molecule is sequenced, a person of skill in the art cannot distinguish a polymerase error artifact from a true mutation (especially rare mutations).

While being able to sequence many different DNA molecules collectively is advantageous in terms of cost and time, the price for this efficiency and convenience is that various PCR errors complicate mutational analysis as long as their frequency is comparable to that of mutations arising in vivo—in other words, genuine in vivo mutations will be essentially indistinguishable from changes that are artifacts of PCR or sequencing errors.

Thus, the present disclosure, in a further aspect, provides methods for identifying mutations present before amplification or sequencing of a double-stranded nucleic acid library wherein the target molecules include a single double-stranded cypher or dual cyphers (i.e., barcodes or identifier tags), one on each end, so that sequencing each complementary strand can be connected back to the original molecule. In certain embodiments, the method enhances the sensitivity of the sequencing method such that the error rate is $5 \times 10^{-6}$, $10^{-6}$, $5 \times 10^{-7}$, $10^{-7}$, $5 \times 10^{-8}$, $10^{-8}$ or less when sequencing many different target nucleic acid molecules simultaneously or such that the error rate is $5 \times 10^{-7}$, $10^{-7}$, $5 \times 10^{-8}$, $10^{-8}$ or less when sequencing a single target nucleic acid molecule in depth.

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the terms "about" and "consisting essentially of" mean ±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

As used herein, the term "random cypher" or "cypher" or "barcode" or "identifier tag" and variants thereof are used interchangeably and refer to a nucleic acid molecule having a length ranging from about 5 to about 50 nucleotides. In certain embodiments, all of the nucleotides of the cypher are not identical (i.e., comprise at least two different nucleotides) and optionally do not contain three contiguous nucleotides that are identical. In further embodiments, the cypher is comprised of about 5 to about 15 nucleotides, about 6 to about 10 nucleotides, and preferably about 7 to about 12 nucleotides. Cyphers will generally be located at one or both ends a target molecule may, which may be incorporated directly onto target molecules of interest or onto a vector into which target molecules will be later added.

As used herein, "target nucleic acid molecules" and variants thereof refer to a plurality of double-stranded nucleic acid molecules that may be fragments or shorter molecules generated from longer nucleic acid molecules, including from natural samples (e.g., a genome), or the target nucleic acid molecules may be synthetic (e.g., cDNA), recombinant, or a combination thereof. Target nucleic acid fragments from longer molecules may be generated using a variety of techniques known in the art, such as mechanical shearing or specific cleavage with restriction endonucleases.

As used herein, a "nucleic acid molecule library" and variants thereof refers to a collection of nucleic acid molecules or fragments. In certain embodiments, the collection of nucleic acid molecules or fragments is incorporated into a vector, which can be transformed or transfected into an appropriate host cell. The target nucleic acid molecules of this disclosure may be introduced into a variety of different vector backbones (such as plasmids, cosmids, viral vectors, or the like) so that recombinant production of a nucleic acid molecule library can be maintained in a host cell of choice (such as bacteria, yeast, mammalian cells, or the like).

For example, a collection of nucleic acid molecules representing the entire genome is called a genomic library and a collection of DNA copies of messenger RNA is referred to as a complimentary DNA (cDNA) library. Methods for introducing nucleic acid molecule libraries into vectors are well known in the art (see, e.g., Current Protocols in Molecular Biology, Ausubel et al., Eds., Greene Publishing and Wiley-Interscience, New York, 1995; Sambrook et al., Molecular Cloning: A Laboratory Manual, 2nd Ed., Cold Spring Harbor Laboratory Vols. 1-3, 1989; Methods in Enzymology, Vol. 152, Guide to Molecular Cloning Techniques, Berger and Kimmel, Eds., San Diego: Academic Press, Inc., 1987).

Depending on the type of library to be generated, the ends of the target nucleic acid fragments may have overhangs or may be "polished" (i.e., blunted). Together, the target nucleic acid molecule fragments can be, for example, cloned directly into a cypher vector to generate a vector library, or be ligated with adapters to generate, for example, polonies. The target nucleic acid molecules, which are the nucleic acid molecules of interest for amplification and sequencing, may range in size from a few nucleotides (e.g., 50) to many thousands (e.g., 10,000). Preferably, the target fragments in the library range in size from about 100 nucleotides to about 750 nucleotides or about 1,000 nucleotides, or from about 150 nucleotides to about 250 nucleotides or about 500 nucleotides.

As used herein, a "nucleic acid molecule priming site" or "PS" and variants thereof are short, known nucleic acid sequences contained in the vector. A PS sequence can vary in length from 5 nucleotides to about 50 nucleotides in length, about 10 nucleotides to about 30 nucleotides, and preferably are about 15 nucleotides to about 20 nucleotides in length. In certain embodiments, a PS sequence may be included at the one or both ends or be an integral part of the random cypher nucleic acid molecules, or be included at the one or both ends or be an integral part of an adapter sequence, or be included as part of the vector. A nucleic acid molecule primer that is complementary to a PS included in a library of the present disclosure can be used to initiate a sequencing reaction.

For example, if a random cypher only has a PS upstream (5') of the cypher, then a primer complementary to the PS can be used to prime a sequencing reaction to obtain the sequence of the random cypher and some sequence of a target nucleic acid molecule cloned downstream of the cypher. In another example, if a random cypher has a first PS upstream (5') and a second PS downstream (3') of the cypher, then a primer complementary to the first PS can be used to prime a sequencing reaction to obtain the sequence of the random cypher, the second PS and some sequence of a target nucleic acid molecule cloned downstream of the second PS. In contrast, a primer complementary to the second PS can be used to prime a sequencing reaction to directly obtain the sequence of the target nucleic acid molecule cloned downstream of the second PS. In this latter case, more target molecule sequence information will be obtained since the sequencing reaction beginning from the second PS can extend further into the target molecule than does the reaction having to extend through both the cypher and the target molecule.

As used herein, "next generation sequencing" refers to high-throughput sequencing methods that allow the sequencing of thousands or millions of molecules in parallel. Examples of next generation sequencing methods include sequencing by synthesis, sequencing by ligation, sequencing by hybridization, polony sequencing, and pyrosequencing. By attaching primers to a solid substrate and a complementary sequence to a nucleic acid molecule, a nucleic acid molecule can be hybridized to the solid substrate via the primer and then multiple copies can be generated in a discrete area on the solid substrate by using polymerase to amplify (these groupings are sometimes referred to as polymerase colonies or polonics). Consequently, during the sequencing process, a nucleotide at a particular position can be sequenced multiple times (e.g., hundreds or thousands of times)—this depth of coverage is referred to as "deep sequencing."

As used herein, "base calling" refers to the computational conversion of raw or processed data from a sequencing instrument into quality scores and then actual sequences. For example, many of the sequencing platforms use optical detection and charge coupled device (CCD) cameras to generate images of intensity information (i.e., intensity information indicates which nucleotide is in which position of a nucleic acid molecule), so base calling generally refers to the computational image analysis that converts intensity data into sequences and quality scores. Another example is the ion torrent sequencing technology, which employs a proprietary semiconductor ion sensing technology to detect release of hydrogen ions during incorporation of nucleotide bases in sequencing reactions that take place in a high density array of micro-machined wells. There are other examples of methods known in the art that may be employed for simultaneous sequencing of large numbers of nucleotide molecules. Various base calling methods are described in, for example, Niedringhaus et al. (*Anal. Chem.* 83:4327, 2011), which methods are herein incorporated by reference in their entirety.

In the following description, certain specific details are set forth in order to provide a thorough understanding of various embodiments of this disclosure. However, upon reviewing this disclosure, one skilled in the art will understand that the invention may be practiced without many of these details. In other instances, newly emerging next generation sequencing technologies, as well as well-known or widely available next generation sequencing methods (e.g., chain-termination sequencing, dye-terminator sequencing, reversible dye-terminator sequencing, sequencing by synthesis, sequencing by ligation, sequencing by hybridization, polony sequencing, pyrosequencing, ion semiconductor sequencing, nanoball sequencing, nanopore sequencing, single molecule sequencing, FRET sequencing, base-heavy sequencing, and microfluidic sequencing), have not all been described in detail to avoid unnecessarily obscuring the descriptions of the embodiments of the present disclosure. Descriptions of some of these methods, which methods are herein incorporated by reference in their entirety, can be found, for example, in PCT Publication Nos. WO 98/44151, WO 00/18957, and WO 2006/08413; and U.S. Pat. Nos. 6,143,496, 6,833,246, and 7,754,429; and U.S. Patent Application Publication Nos. U.S. 2010/0227329 and U.S. 2009/0099041.

Various embodiments of the present disclosure are described for purposes of illustration, in the context of use with vectors containing a library of nucleic acid fragments (e.g., genomic or cDNA library). However, as those skilled in the art will appreciate upon reviewing this disclosure, use with other nucleic acid libraries or methods for making a library of nucleic acid fragments may also be suitable.

In certain embodiments, a double-stranded nucleic acid library comprises a plurality of target nucleic acid molecules and a plurality of random cyphers, wherein the nucleic acid library comprises molecules having a formula of $X^a$—Y—$X^b$ (in 5' to 3' order), wherein (a) $X^a$ comprises a first random cypher, (b) Y comprises a target nucleic acid molecule, and (c) $X^b$ comprises a second random cypher; wherein each of the plurality of random cyphers have a length of about 5 to about 50 nucleotides. In certain embodiments, the double-stranded sequence of the $X^a$ cypher for each target nucleic acid molecule is different from the double-stranded sequence of the $X^b$ cypher. In certain other embodiments, the double-stranded $X^a$ cypher is identical to the $X^b$ cypher for one or more target nucleic acid molecules, provided that the double-stranded cypher for each target nucleic acid molecule is different.

In further embodiments, the plurality or pool of random cyphers used in the double-stranded nucleic acid molecule library or vector library comprise from about 5 nucleotides to about 40 nucleotides, about 5 nucleotides to about 30 nucleotides, about 6 nucleotides to about 30 nucleotides, about 6 nucleotides to about 20 nucleotides, about 6 nucleotides to about 10 nucleotides, about 6 nucleotides to about 8 nucleotides, about 7 nucleotides to about 9 or about 10 nucleotides, or about 6, about 7 or about 8 nucleotides. In certain embodiments, a cypher preferably has a length of about 6, about 7, about 8, about 9, about 10, about 11, about 12, about 13, about 14, about 15, about 16, about 17, about 18, about 19, or about 20 nucleotides. In certain embodiments, a pair of random cyphers associated with nucleic acid sequences or vectors will have different lengths or have the same length. For example, a target nucleic acid molecule or vector may have an upstream (5') first random cypher of about 6 nucleotides in length and a downstream (3') second random cypher of about 9 nucleotides in length, or a target nucleic acid molecule or vector may have an upstream (5') first random cypher of about 7 nucleotides in length and a downstream (3') second random cypher of about 7 nucleotides in length.

In certain embodiments, both the $X^a$ cypher and the $X^b$ cypher each comprise 6 nucleotides, 7 nucleotides, 8 nucleotides, 9 nucleotides, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, or 20 nucleotides. In certain other embodiments, the $X^a$ cypher comprises 6 nucleotides and the $X^b$ cypher comprises 7 nucleotides or 8 nucleotides; or the $X^a$ cypher comprises 7 nucleotides and the $X^b$ cypher comprises 6 nucleotides or 8 nucleotides; or the $X^a$ cypher comprises 8 nucleotides and the $X^b$ cypher comprises 6 nucleotides or 7 nucleotides; or the $X^a$ cypher comprises 10 nucleotides and the $X^b$ cypher comprises 11 nucleotides or 12 nucleotides.

The number of nucleotides contained in each of the random cyphers or barcodes will govern the total number of possible barcodes available for use in a library. Shorter barcodes allow for a smaller number of unique cyphers, which may be useful when performing a deep sequence of one or a few nucleotide sequences, whereas longer barcodes may be desirable when examining a population of nucleic acid molecules, such as cDNAs or genomic fragments. In certain embodiments, multiplex sequencing may be desired when targeting specific nucleic acid molecules, specific genomic regions, smaller genomes, or a subset of cDNA transcripts. Multiplex sequencing involves amplifying two or more samples that have been pooled into, for example, a single lane of a flow cell for bridge amplification to exponentially increase the number of molecules analyzed in a single run without sacrificing time or cost. In related embodiments, a unique index sequence (comprising a length ranging from about 4 nucleotides to about 25 nucleotides) specific for a particular sample is included with each dual cypher vector library. For example, if ten different samples are being pooled in preparation for multiplex sequencing, then ten different index sequences will be used such that ten dual cypher vector libraries are used in which each library has a single, unique index sequence identifier (but each library has a plurality of random cyphers).

For example, a barcode of 7 nucleotides would have a formula of 5'-N-3' (SEQ ID NO.:1), wherein N may be any naturally occurring nucleotide. The four naturally occurring nucleotides are A, T, C, and G, so the total number of possible random cyphers is $4^7$, or 16,384 possible random arrangements (i.e., 16,384 different or unique cyphers). For 6 and 8 nucleotide barcodes, the number of random cyphers would be 4,096 and 65,536, respectively. In certain embodiments of 6, 7 or 8 random nucleotide cyphers, there may be fewer than the pool of 4,094, 16,384 or 65,536 unique cyphers, respectively, available for use when excluding, for example, sequences in which all the nucleotides are identical (e.g., all A or all T or all C or all G) or when excluding sequences in which three contiguous nucleotides are identical or when excluding both of these types of molecules. In addition, the first about 5 nucleotides to about 20 nucleotides of the target nucleic acid molecule sequence may be used as a further identifier tag together with the sequence of an associated random cypher.

In still further embodiments, a double-stranded nucleic acid library comprises a plurality of target nucleic acid molecules and a plurality of random cyphers, wherein the nucleic acid library comprises molecules having a formula of $X^a$—Y—$X^b$ (in 5' to 3' order), wherein (a) $X^a$ comprises a first random cypher, (b) Y comprises a target nucleic acid molecule, and (c) $X^b$ comprises a second random cypher; wherein each of the plurality of random cyphers have a length of about 5 to about 50 nucleotides and wherein (i) at least two of those nucleotides are different in each cypher or (ii) each cypher does not contain three contiguous nucleotides that are identical. In certain embodiments wherein each cypher does not contain three contiguous nucleotides that are identical, the double-stranded $X^a$ cypher is identical to the $X^b$ cypher for one or more target nucleic acid molecules, provided that the double-stranded cypher for each target nucleic acid molecule is different.

In yet further embodiments, a double-stranded nucleic acid library comprises a plurality of target nucleic acid molecules and a plurality of random cyphers, wherein the nucleic acid library comprises molecules having a formula of $X^a$—$X^b$—Y, $X^b$—$X^a$—Y, Y—$X^a$—$X^b$, Y—$X^b$—$X^a$, $X^a$—Y, $X^b$—Y, Y—$X^a$, or Y—$X^b$ (in 5' to 3' order), wherein (a) $X^a$ comprises a first random cypher, (b) Y comprises a target nucleic acid molecule, and (c) $X^b$ comprises a second random cypher; wherein each of the plurality of random cyphers have a length of about 5 to about 50 nucleotides.

In any of the embodiments described herein, an $X^a$ cypher further comprises about a 5 nucleotide to about a 20 nucleotide sequence of the target nucleic acid molecule that is downstream of the $X^a$ cypher, or an $X^b$ cypher further comprises about a 5 nucleotide to about a 20 nucleotide sequence of the target nucleic acid molecule that is upstream of the $X^b$ cypher, or an $X^a$ cypher and $X^b$ cypher further comprise about a 5 nucleotide to about a 20 nucleotide sequence of the target nucleic acid molecule that is downstream or upstream, respectively, of each cypher.

In yet further embodiments, a first target molecule is associated with and disposed between a first random cypher $X^a$ and a second random cypher $X^b$, a second target molecule is associated with and disposed between a third random cypher $X^a$ and a fourth random cypher $X^b$, and so on, wherein the target molecules of a library or of a vector library each has a unique $X^a$ cypher (i.e., none of the $X^a$ cyphers have the same sequence) and each has a unique $X^b$ cypher (i.e., none of the $X^b$ cyphers have the same sequence), and wherein none or only a minority of the $X^a$ and $X^b$ cyphers have the same sequence.

For example, if the length of the random cypher is 7 nucleotides, then there will a total of 16,384 different barcodes available as first random cypher $X^a$ and second random cypher $X^b$. In this case, if a first target nucleic acid molecule is associated with and disposed between random cypher $X^a$ number 1 and random cypher $X^b$ number 2 and a second target nucleic acid molecule is associated with and disposed between random cypher $X^a$ number 16,383 and random cypher $X^b$ number 16,384, then a third target nucleic acid molecule can only be associated with and disposed between any pair of random cypher numbers selected from numbers 3 to 16,382, and so on for each target nucleic acid molecule of a library until each of the different random cyphers have been used (which may or may not be all 16,382). In this embodiment, each target nucleic acid molecule of a library will have a unique pair of cyphers that differ from each of the other pairs of cyphers found associated with each other target nucleic acid molecule of the library.

In any of the embodiments described herein, random cypher sequences from a particular pool of cyphers (e.g., pools of 4,094, 16,384 or 65,536 unique cyphers) may be used more than once. In further embodiments, each target nucleic acid molecule or a subset of target molecules has a different (unique) pair of cyphers. For example, if a first target molecule is associated with and disposed between random cypher number 1 and random cypher number 100, then a second target molecule will need to be flanked by a different dual pair of cyphers—such as random cypher number 1 and random cypher number 65, or random cypher number 486 and random cypher number 100—which may be any combination other than 1 and 100. In certain other embodiments, each target nucleic acid molecule or a subset of target molecules has identical cyphers on each end of one or more target nucleic acid molecules, provided that the double-stranded cypher for each target nucleic acid molecule is different. For example, if a first target molecule is flanked by cypher number 10, then a second target molecule having identical cyphers on each end will have to have a different cypher—such as random cypher number 555 or the like—which may be any other cypher other than 10. In still further embodiments, target nucleic acid molecules of the nucleic acid molecule library will each have dual unique cyphers $X^a$ and $X^b$, wherein none of the $X^a$ cyphers have the same sequence as any other $X^a$ cypher, none of the $X^b$ cyphers have the same sequence as any other $X^b$ cypher, and none of the $X^a$ cyphers have the same sequence as any $X^b$ cypher. In still further embodiments, target nucleic acid molecules of the nucleic acid molecule library will each have a unique pair of $X^a$—$X^b$ cyphers wherein none of the $X^a$ or $X^b$ cyphers have the same sequence. A mixture of any of the aforementioned embodiments may make up a nucleic acid molecule library of this disclosure.

In any of the embodiments described herein, the plurality of target nucleic acid molecules that together are used to generate a nucleic acid molecule library (or used for insertion into a vector to generate a vector library containing a plurality of target nucleic acid molecules) may each have a length that ranges from about 10 nucleotides to about 10,000 nucleotides, from about 50 nucleotides to about 5,000 nucleotides, from about 100 nucleotides to about 1,000 nucleotides, or from about 150 nucleotides to about 750 nucleotides, or from about 250 nucleotides to about 500 nucleotides.

In any of the embodiments described herein, the plurality of random cyphers may further be linked to a first nucleic acid molecule priming site (PS1), linked to a second nucleic acid molecule priming site (PS2), or linked to both a first and a second nucleic acid molecule priming site. In certain embodiments, a plurality of random cyphers may each be associated with and disposed between a first nucleic acid molecule priming site (PS1) and a second nucleic acid molecule priming site (PS2), wherein the double-stranded sequence of PS1 is different from the double-stranded sequence of PS2. In certain embodiments, each pair of $X^a$—$X^b$ cyphers may be associated with and disposed between an upstream and a downstream nucleic acid molecule priming site (PS1) (see, e.g., FIG. 2).

In any of the embodiments described herein, a first nucleic acid molecule priming site PS1 will be located upstream (5') of the first random cypher $X^a$ and the first nucleic acid molecule priming site PS1 will also be located downstream (3') of the second random cypher $X^b$. In certain embodiments, an oligonucleotide primer complementary to the sense strand of PS1 can be used to prime a sequencing reaction to obtain the sequence of the sense strand of the first random cypher $X^a$ or to prime a sequencing reaction to obtain the sequence of the anti-sense strand of the second random cypher $X^b$, whereas an oligonucleotide primer complementary to the anti-sense strand of PS1 can be used to prime a sequencing reaction to obtain the sequence of the anti-sense strand of the first random cypher $X^a$ or to prime a sequencing reaction to obtain the sequence of the sense strand of the second random cypher $X^b$.

In any of the embodiments described herein, the second nucleic acid molecule priming site PS2 will be located downstream (3') of the first random cypher $X^a$ and the second nucleic acid molecule priming site PS2 will also be located upstream (5') of the second random cypher $X^b$. In certain embodiments, an oligonucleotide primer complementary to the sense strand of PS2 can be used to prime a sequencing reaction to obtain the sequence of the sense strand from the 5'-end of the associated double-stranded target nucleic acid molecule or to prime a sequencing reaction to obtain the sequence of the anti-sense strand from the 3'-end of the associated double-stranded target nucleic acid molecule, whereas an oligonucleotide primer complementary to the anti-sense strand of PS2 can be used to prime a sequencing reaction to obtain the sequence of the anti-sense strand from the 5'-end of the associated double-stranded target nucleic acid molecule or to prime a sequencing reaction to obtain the sequence of the sense strand from the 3'-end of the associated double-stranded target nucleic acid molecule.

Depending on the length of the target nucleic acid molecule, the entire target nucleic acid molecule sequence may be obtained if it is short enough or only a portion of the entire target nucleic acid molecule sequence may be obtained if it is longer than about 100 nucleotides to about 250 nucleotides. An advantage of the compositions and methods of the instant disclosure is that even though a target nucleic acid molecule is too long to obtain sequence data for the entire molecule or fragment, the sequence data obtained from one end of a double-stranded target molecule can be specifically linked to sequence data obtained from the opposite end or from the second strand of that same double-stranded target molecule because each target molecule in a library of this disclosure will have double-stranded cyphers, or a unique $X^a$—$X^b$ pair of cyphers. Linking the sequence data of the two strands allows for sensitive identification of "true" mutations wherein deeper sequencing actually increases the sensitivity of the detection, and these methods can provide sufficient data to quantify the number of artifact mutations.

In any of the embodiments described herein, a plurality of random cyphers may further comprise a first restriction endonuclease recognition sequence (RE1) and a second restriction endonuclease recognition sequence (RE2), wherein the first restriction endonuclease recognition sequence RE1 is located upstream (5') of the first random cypher $X^a$ and the second restriction endonuclease recognition sequence RE2 is located downstream (3') of the second random cypher $X^b$. In certain embodiments, a first restriction endonuclease recognition sequence RE1 and a second restriction endonuclease recognition sequence RE2 are the same or different. In certain embodiments, RE1, RE2, or both RE1 and RE2 are "rare-cutter" restriction endonucleases that have a recognition sequence that occurs only rarely within a genome or within a target nucleic acid molecule sequence or are "blunt-cutters" that generate nucleic acid molecules with blunt ends after digestion (e.g., SmaI). Such rare cutter enzymes generally have longer recognition sites with seven- or eight-nucleotide or longer recognition sequences, such as AarI, AbeI, AscI, AsiSI, BbvCI, BstRZ2461, BstSWI, Cc/NI, CsiBI, CspBI, FseI, NotI, MchA1, MspSWI, MssI, PacI, PmeI, SbfI, SdaI, SgfI, SmiI, SrfI, Sse232I, Sse8387I, SwaI, TaqII, VpaK32I, or the like.

In certain embodiments, a nucleic acid molecule library comprises nucleic acid molecules having a formula of 5'-RE1-PS1-$X^a$-PS2-Y-PS2-$X^b$-PS1-RE2-3', wherein RE1 is a first restriction endonuclease recognition sequence, PS1 is a first nucleic acid molecule priming site, PS2 is a second nucleic acid molecule priming site, RE2 is a second restriction endonuclease recognition sequence, Y comprises a target nucleic acid molecule, and $X^a$ and $X^b$ are cyphers comprising a length ranging from about 5 nucleotides to about 50 nucleotides or about 6 nucleotides to about 15 nucleotides or about 7 nucleotides to about 9 nucleotides. In further embodiments, RE1 and RE2 are sequences recognized by the same restriction endonuclease or an isoschizomer or neoschizomer thereof, or RE1 and RE2 have different sequences recognized by different restriction endonucleases. In further embodiments, PS1 and PS2 have different sequences. In further embodiments, target nucleic acid molecules of the nucleic acid molecule library will each have dual unique cyphers $X^a$ and $X^b$, wherein none of the $X^a$ cyphers have the same sequence as any other $X^a$ cypher, none of the $X^b$ cyphers have the same sequence as any other $X^b$ cypher, and none of the $X^a$ cyphers have the same sequence as any $X^b$ cypher. In still further embodiments, target nucleic acid molecules of the nucleic acid molecule library will each have a unique cypher or pair of $X^a$—$X^b$ cyphers wherein none of the $X^a$ or $X^b$ cyphers have the same sequence.

Also contemplated in the present disclosure is using a library of double-stranded barcoded or dual double-stranded barcoded target nucleic acid molecules for amplification and sequencing reactions to detect true mutations. In order to facilitate certain amplification or sequencing methods, other features may be included in the compositions of the instant disclosure. For example, bridge amplification may involve ligating adapter sequences to each end of a population of target nucleic acid molecules. Single-stranded oligonucleotide primers complementary to the adapters are immobilized on a solid substrate, the target molecules containing the adapter sequences are denatured into single strands, and hybridized to complementary primers on the solid substrate. An extension reaction is used to copy the hybridized target molecule and the double-stranded product is denatured into single strands again. The copied single strands then loop over (form a "bridge") and hybridize with a complementary primer on the solid substrate, upon which the extension reaction is run again. In this way, many target molecules may be amplified at the same time and the resulting product is subject to massive parallel sequencing.

In certain embodiments, a nucleic acid molecule library comprises nucleic acid molecules having a formula of 5'-RE1-AS-PS1-$X^a$-PS2-Y-PS2-$X^b$-PS1-AS-RE2-3', wherein RE1 and RE2 are first and second restriction endonuclease recognition sequences, PS1 and PS2 are a first and second nucleic acid molecule priming sites, AS is an adapter sequence comprising a length ranging from about 20 nucleotides to about 100 nucleotides, Y comprises a target nucleic acid molecule, and $X^a$ and $X^b$ are cyphers comprising a length ranging from about 5 nucleotides to about 50 nucleotides or about 6 nucleotides to about 15 nucleotides or about 7 nucleotides to about 9 nucleotides.

In further embodiments, a nucleic acid molecule library comprises nucleic acid molecules having a formula of 5'-RE1-AS-PS1-$X^a$—Y—$X^b$-PS1-AS-RE2-3', wherein RE1 and RE2 are first and second restriction endonuclease recognition sequences, PS1 is a first nucleic acid molecule priming site, AS is an adapter sequence comprising a length ranging from about 20 nucleotides to about 100 nucleotides, Y comprises a target nucleic acid molecule, and $X^a$ and $X^b$ are cyphers comprising a length ranging from about 5 nucleotides to about 50 nucleotides or about 6 nucleotides to about 15 nucleotides or about 7 nucleotides to about 9 nucleotides. In related embodiments, the AS adapter sequence of the aforementioned vector may further comprise a PS2 that is a second nucleic acid molecule priming site or the PS2 may be a part of the original AS sequence. In still further embodiments, the nucleic acid molecule library may further comprise an index sequence (comprising a length ranging from about 4 nucleotides to about 25 nucleotides) located between each of the first and second AS and the PS1 so that the library can be pooled with other libraries having different index sequences to facilitate multiplex sequencing (also referred to as multiplexing) either before or after amplification.

Each of the aforementioned dual barcoded target nucleic acid molecules may be assembled into a carrier library in the form of, for example, a self-replicating vector, such as a plasmid, cosmid, YAC, viral vector or other vectors known in the art. In certain embodiments, any of the aforementioned double-stranded nucleic acid molecules comprising a plurality of target nucleic acid molecules and a plurality of random cyphers, are contained in a vector. In still further embodiments, such a vector library is carried in a host cell, such as bacteria, yeast, or mammalian cells.

Figure 2:
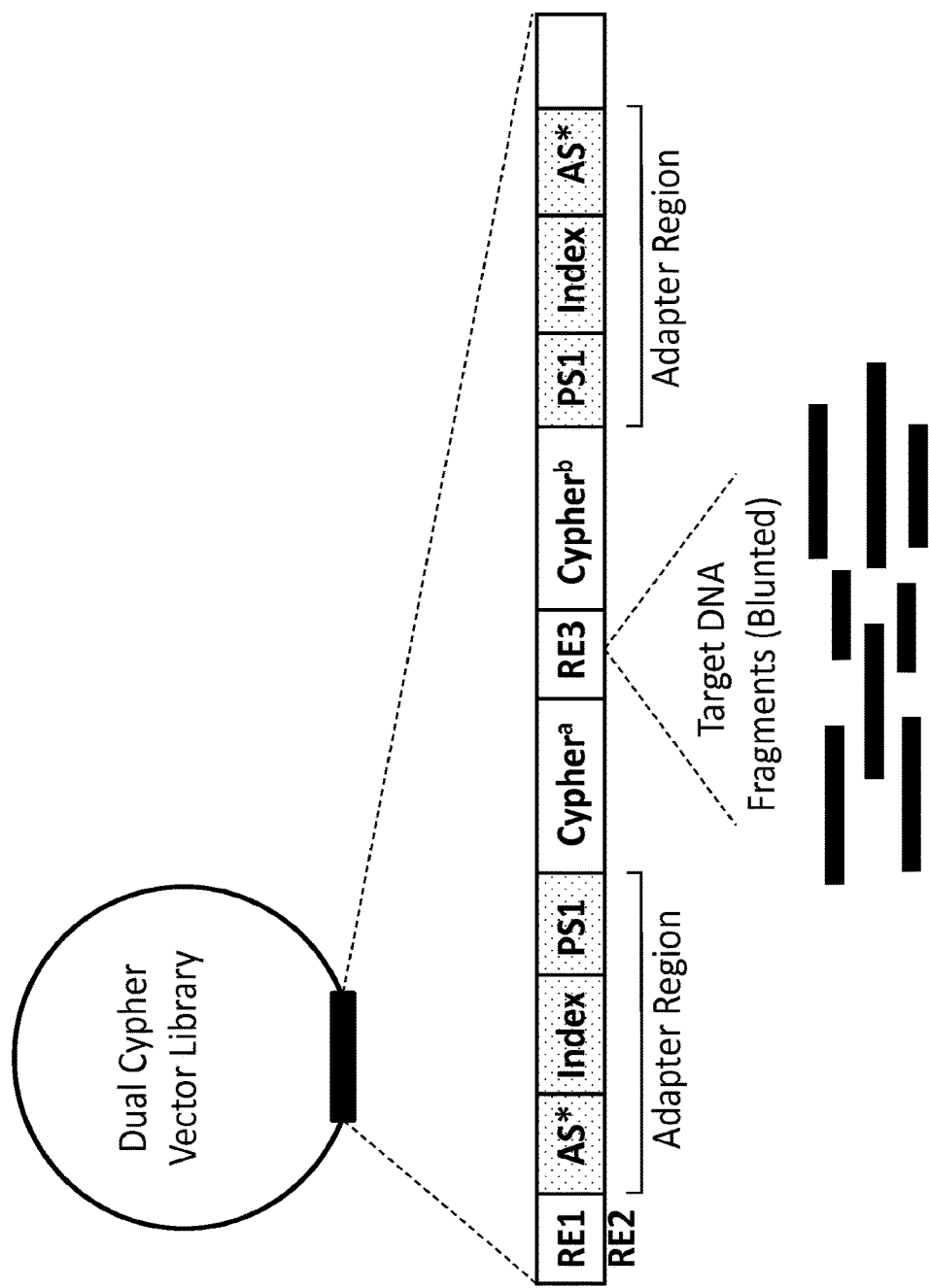
FIG. 2 is a cartoon illustration of an exemplary vector of the present disclosure, wherein adaptor sequences are included and are useful for, for example, bridge amplification methods before sequencing.
Figure 3A:
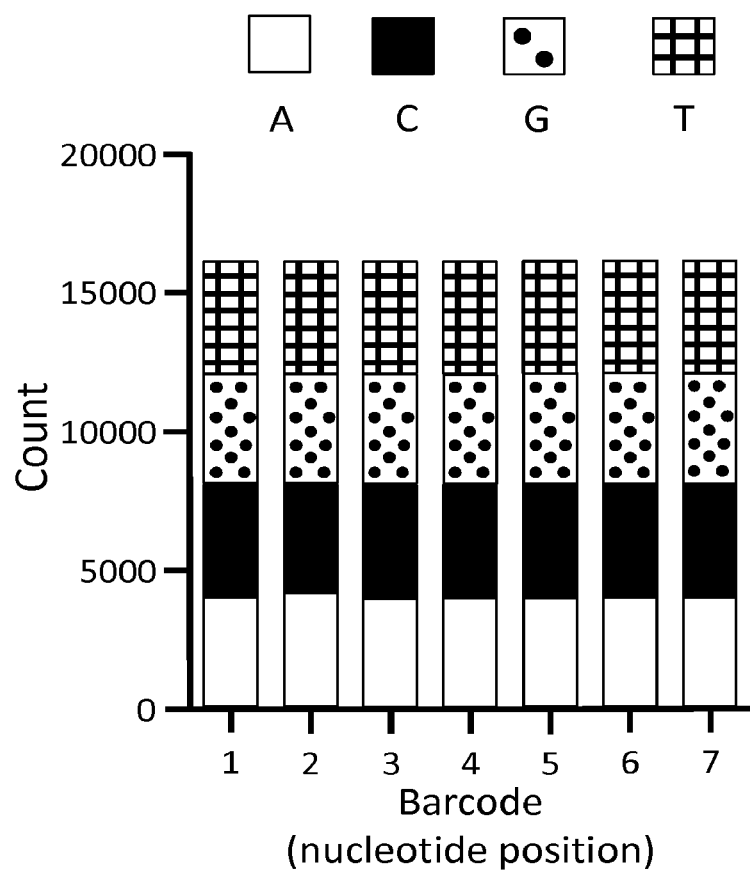
FIGS. 3A and 3B show characteristics of a cypher library and the detection of true mutations. (A) Data generated in a single next generation sequence run on MiSeq® demonstrates broad coverage and diversity at the upstream seven base pair cypher in a vector library, wherein the vector used is illustrated in FIG. 2. (B) Cypher Seq eliminates errors introduced during library preparation and sequencing. Target nucleic acid molecules were ligated into a cypher vector library containing previously catalogued dual, double-stranded cyphers. The target sequences were amplified and sequenced. All sequencing reads having identical cypher pairs, along with their reverse complements, were grouped into families. Comparison of family sequences allowed for generation of a consensus sequence wherein 'mutations' (errors) arising during library preparation (open circle) and during sequencing (gray circle and triangle) were computationally eliminated. Generally, mutations that are present in all or substantially all reads (black diamond) from the same cypher and its reverse complement are counted as true mutations.
Figure 3B:
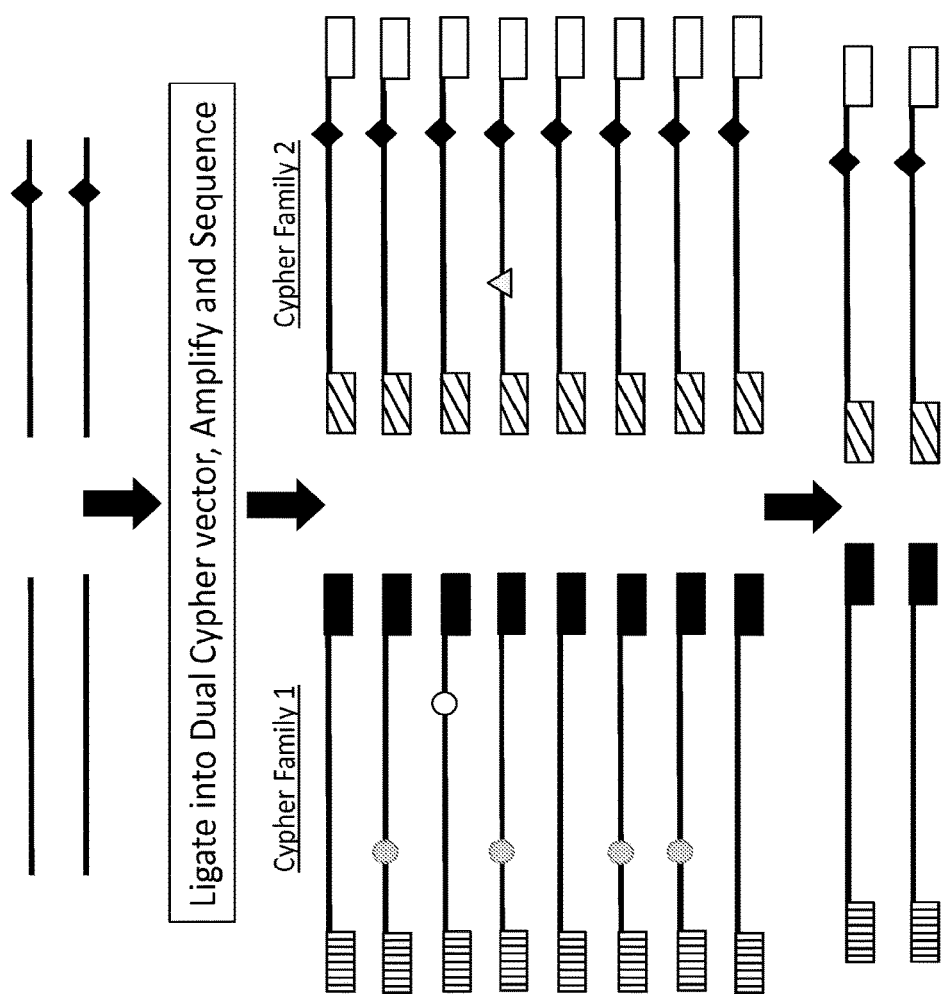
Figure 4A:
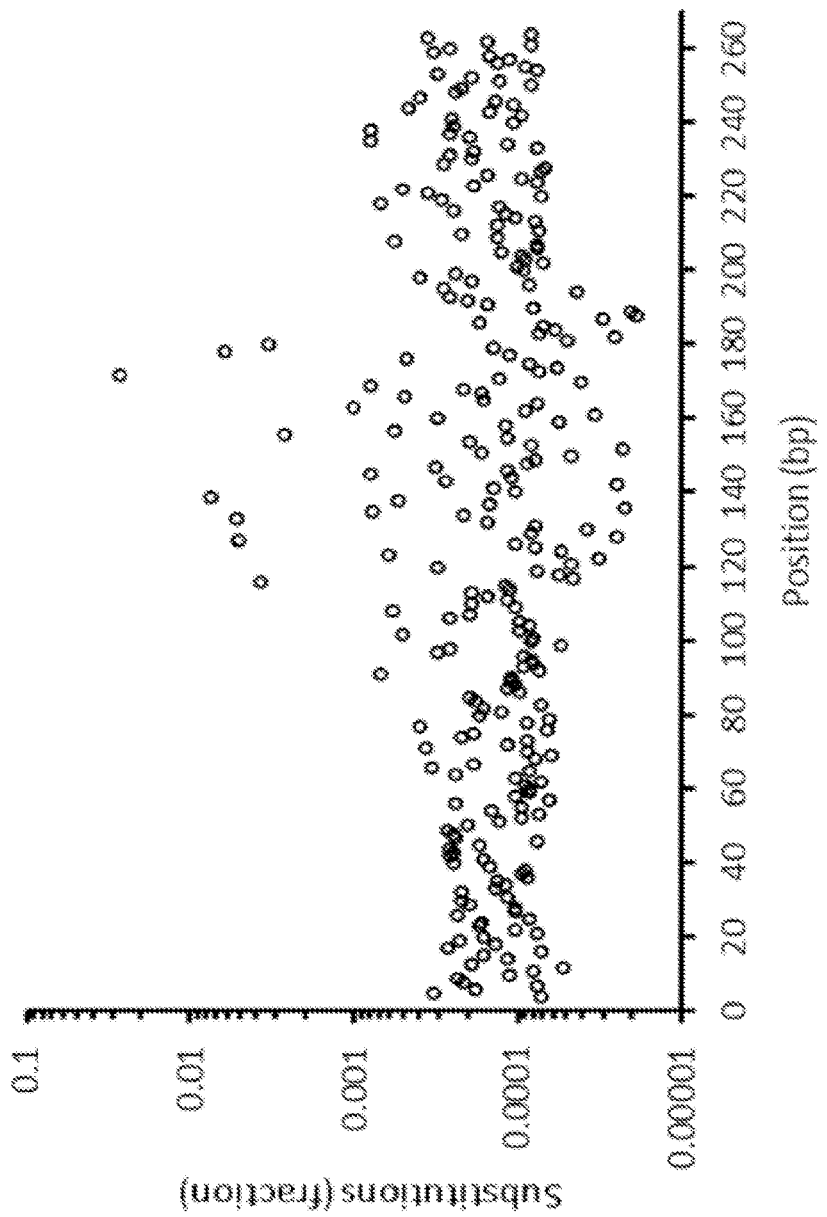
FIGS. 4A and 4B show that the cypher system can distinguish true mutations from artifact mutations. (A) Wild-type TP53 Exon 4 was ligated into a library of Cypher Seq vectors and sequenced on the Illumina MiSeq® instrument with a depth of over a million. Sequences were then compared to wild-type TP53 sequence. Detected substitutions were plotted before (A) and after correction (B) with Cypher Seq.
Figure 4B:
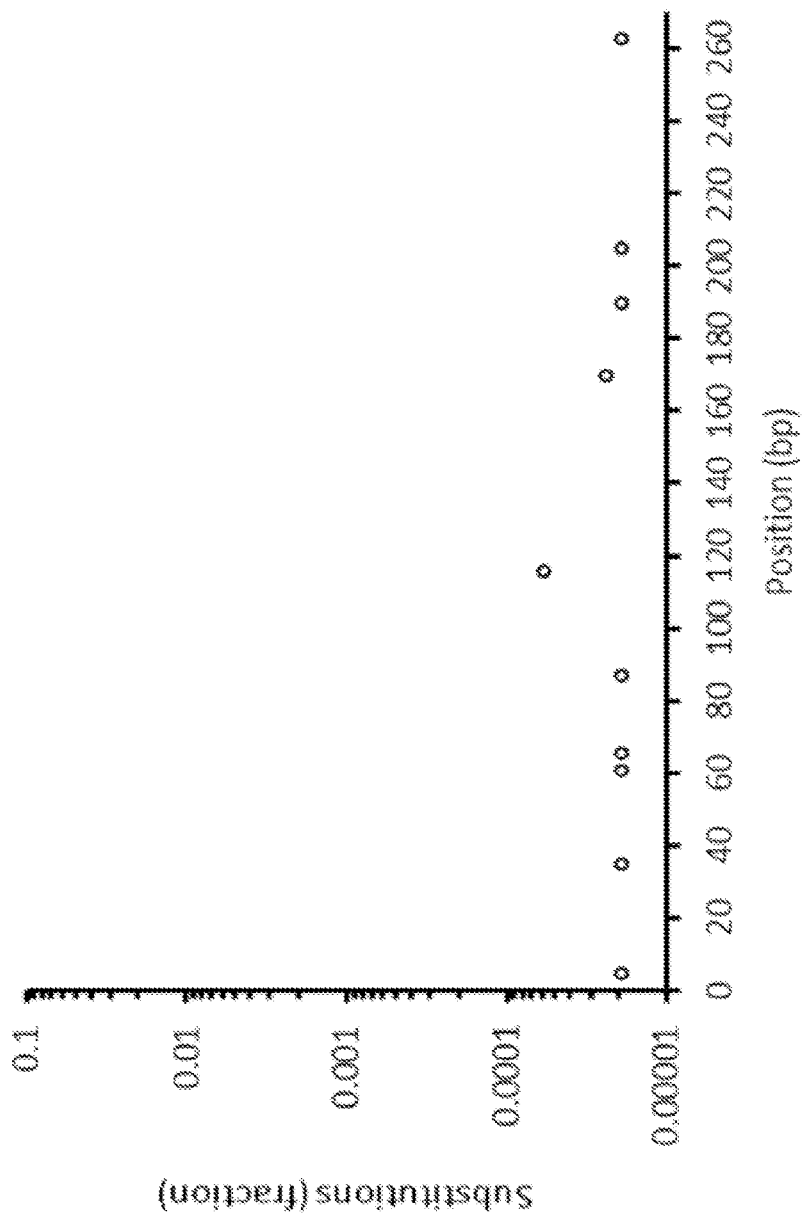

The present disclosure also provides vectors useful for generating a library of dual barcoded target nucleic acid molecules according to this disclosure. Exemplary vectors comprising cyphers and other elements of this disclosure are illustrated in FIGS. 1 and 2.

In certain embodiments, there are provided a plurality of nucleic acid vectors, comprising a plurality of random cyphers, wherein each vector comprises a region having a formula of 5'-RE1-PS1-$X^a$-PS2-RE3-PS2-$X^b$-PS1-RE2-3 wherein (a) RE1 is a first restriction endonuclease recognition sequence, (b) PS1 is a first nucleic acid molecule priming site, (c) $X^a$ comprises a first random cypher, (d) RE3 is a third restriction endonuclease recognition sequence, wherein RE3 is a site into which a target nucleic acid molecule can be inserted, (e) $X^b$ comprises a second random cypher, (f) PS2 is a second nucleic acid molecule priming site, and (g) RE2 is a second restriction endonuclease recognition sequence; and wherein each of the plurality of random cyphers comprise a length ranging from about 5 nucleotides to about 50 nucleotides, preferably from about 7 nucleotides to about 9 nucleotides; and wherein the plurality of nucleic acid vectors are useful for preparing a double-stranded nucleic acid molecule library in which each vector has a different target nucleic acid molecule insert. In certain embodiments, the sequence of the $X^a$ cypher is different from the sequence of the $X^b$ cypher in each vector (that is, each vector has a unique pair). In further embodiments, the plurality of nucleic acid vectors may further comprise at least one adapter sequence (AS) between RE1 and PS1 and at least one AS between PS1 and RE2, or comprise at least one AS between RE1 and $X^a$ cypher and at least one AS between $X^b$ cypher and RE2, wherein the AS optionally has a priming site.

In further vector embodiments, the plurality of random cyphers can each have the same or different number of nucleotides, and comprise from about 6 nucleotides to about 8 nucleotides to about 10 nucleotides to about 12 nucleotides to about 15 nucleotides. In still other embodiments, a plurality of target nucleic acid molecules comprising from about 10 nucleotides to about 10,000 nucleotides or comprising from about 100 nucleotides to about 750 nucleotides or to about 1,000 nucleotides, may be inserted into the vector at RE3. In certain embodiments, RE3 will cleave DNA into blunt ends and the plurality of target nucleic acid molecules ligated into this site will also be blunt-ended.

In certain embodiments, the plurality of nucleic acid vectors wherein each vector comprises a region having a formula of 5'-RE1-PS1-$X^a$-PS2-RE3-PS2-$X^b$-PS1-RE2-3' the $X^a$ cyphers and $X^b$ cyphers on each vector is sequenced before a target nucleic acid molecule is inserted into each vector. In further embodiments, the plurality of nucleic acid vectors wherein each vector comprises a region having a formula of 5'-RE1-PS1-$X^a$-PS2-RE3-PS2-$X^b$-PS1-RE2-3' the $X^a$ cyphers and $X^b$ cyphers on each vector is sequenced after a target nucleic acid molecule is inserted into each vector or is sequenced at the same time a target nucleic acid molecule insert is sequenced.

The dual barcoded target nucleic acid molecules and the vectors containing such molecules of this disclosure may further be used in sequencing reactions to determine the sequence and mutation frequency of the molecules in the library. In certain embodiments, this disclosure provides a method for obtaining a nucleic acid sequence by preparing a double-stranded dual barcoded nucleic acid library as described herein and then sequencing each strand of the plurality of target nucleic acid molecules and plurality of random cyphers. In certain embodiments, target nucleic acid molecules and and associated cyphers are excised for sequencing directly from the vector using restriction endonuclease enzymes prior to amplification. In certain embodiments, next generation sequencing methods are used to determine the sequence of library molecules, such as sequencing by synthesis, pyrosequencing, reversible dye-terminator sequencing or polony sequencing.

In still further embodiments, there are provided methods for determining the error rate due to amplification and sequencing by determining the sequence of one strand of a target nucleic acid molecule associated with the first random cypher and aligning with the sequence of the complementary strand associated with the second random cypher to distinguish between a pre-existing mutation and an amplification or sequencing artifact mutation, wherein the measured sequencing error rate will range from about $10^{-6}$ to about $5\times10^{-6}$ to about $10^{-7}$ to about $5\times10^{-7}$ to about $10^{-8}$ to about $10^{-9}$. In other words, using the methods of this disclosure, a person of ordinary skill in the art can associate each DNA sequence read to an original template DNA. Given that both strands of the original double-stranded DNA are barcoded with associated barcodes, this increases the sensitivity of the sequencing base call by more easily identifying artifact "mutations" sequence changes introduced during the sequencing process.

In certain embodiments, the compositions and methods of this instant disclosure will be useful in detecting rare mutants against a large background signal, such as when monitoring circulating tumor cells; detecting circulating mutant DNA in blood, monitoring or detecting disease and rare mutations by direct sequencing, monitoring or detecting disease or drug response associated mutations. Additional embodiments may be used to quantify DNA damage, quantify or detect mutations in viral genomes (e.g., HIV and other viral infections) or other infectious agents that may be indicative of response to therapy or may be useful in monitoring disease progression or recurrence. In yet other embodiments, these compositions and methods may be useful in detecting damage to DNA from chemotherapy, or in detection and quantitation of specific methylation of DNA sequences.

---

What is claimed is:

1. A method for accurately detecting a true mutation in a nucleic acid molecule, comprising:
amplifying a collection of double-stranded nucleic acids comprising a plurality of target nucleic acid molecules and a plurality of double-stranded cyphers, wherein the double-stranded nucleic acids have a formula of $X^a$—Y—$X^b$ (in 5' to 3' order), wherein:
(a) $X^a$ comprises a first cypher;
(b) Y comprises a target nucleic acid molecule, and
(c) $X^b$ comprises a second cypher,
wherein each of the plurality of cyphers comprises an exogenous polynucleotide ranging from about 5 nucleotides to about 50 nucleotides in length, wherein each strand of the plurality of target nucleic acid molecules and plurality of double-stranded cyphers are amplified;
sequencing each amplified strand of the plurality of target nucleic acid molecules and plurality of cyphers to obtain sequencing reads for each strand of the plurality of target nucleic acid molecules and the plurality of cyphers;
grouping sequencing reads from both strands of a target nucleic acid molecule comprising an identical first and second cypher pair; and
detecting the true mutation over a background rate of artifact mutations, wherein the true mutation is a mutation detected in both strands of a target nucleic acid molecule.

2. The method of claim 1 wherein the plurality of cyphers each have the same number of nucleotides and comprise a length of about 5, 6, 7, 8, 9, 10, 11, 12, 13, 14, 15, 16, 17, 18, 19, or 20 nucleotides.

3. The method of claim 1, wherein the target nucleic acid molecule of Y comprises from about 10 nucleotides to about 10,000 nucleotides or from about 100 nucleotides to about 1,000 nucleotides.

4. The method of claim 1, wherein the amplifying is by bridge amplification, emulsion amplification, nano-ball amplification, or PCR amplification.

5. The method of claim 1, wherein the sequencing is sequencing by synthesis, pyrosequencing, reversible dye-terminator sequencing or polony sequencing.

6. The method of claim 1, wherein the sequence of one strand of a target nucleic acid molecule associated with the first cypher aligned with the sequence of the complementary strand associated with the second cypher results in a measureable sequencing error rate ranging from about $10^{-6}$ to about $10^{-8}$.

7. The method of claim 1, comprising generating a consensus sequence for the grouped sequencing reads.

8. The method of claim 7, wherein generating the consensus sequence comprises computationally eliminating mutations arising during amplifying or during sequencing.

9. The method of claim 1, wherein each target nucleic acid molecule in the collection of double-stranded nucleic acids library is associated with a unique pair of double-stranded first and second cyphers.

10. The method of claim 1, comprising aligning sequencing reads of complementary strands of the same target nucleic acid molecule to detect mutations arising during amplifying or during sequencing.

11. The method of claim 1, wherein the double-stranded sequence of the $X^a$ cypher for each target nucleic acid molecule is different from the double-stranded sequence of the $X^b$ cypher.

12. The method of claim 11, wherein none of the double-stranded sequences of the $X^a$ cypher is the same as the double-stranded sequence of any other $X^a$ cypher, wherein none of the double-stranded sequences of the $X^b$ cypher is the same as the double-stranded sequence of any other $X^b$ cypher, and wherein none of the double-stranded sequences of the $X^a$ cypher and the $X^b$ cypher are the same.

13. The method of claim 1, wherein the double-stranded $X^a$ cypher is identical to the double-stranded $X^b$ cypher for one or more target nucleic acid molecules, provided that the combination of double-stranded cyphers for each target nucleic acid molecule is different.

14. The method of claim 1, wherein detecting the true mutation comprises sequencing the plurality of target nucleic acid molecules with an error rate ranging from about $10^{-6}$ to about $10^{-8}$.

15. The method of claim 1, wherein detecting the true mutation comprises simultaneously sequencing a plurality of different target nucleic acid molecules with an error rate of $5 \times 10^{-6}$ or less, $10^{-6}$ or less, $5 \times 10^{-7}$ or less, $10^{-8}$ or less, $5 \times 10^{-8}$ or less, or $10^{-8}$ or less.

16. The method of claim 1, wherein detecting the true mutation comprises sequencing a single target nucleic acid molecule in depth with an error rate of $5 \times 10^{-7}$ or less, $10^{-7}$ or less, $5 \times 10^{-8}$ or less, or $10^{-8}$ or less.

17. The method of claim 1, wherein the first and/or second cyphers are random cyphers.

18. The method of claim 1, wherein the first and/or second cyphers are cataloged cyphers.

19. The method of claim 1, wherein the first and/or second cyphers are cataloged random cyphers.

20. The method of claim 1, wherein the sequencing reads do not cover the entire sequence of a double-stranded target nucleic acid molecule.

21. The method of claim 20, wherein none of the double-stranded sequences of the $X^a$ cypher is the same as the double-stranded sequence of any other $X^a$ cypher, wherein none of the double-stranded sequences of the $X^b$ cypher is the same as the double-stranded sequence of any other $X^b$ cypher, and wherein none of the double-stranded sequences of the $X^a$ cypher and the $X^b$ cypher are the same.

22. The method of claim 20, comprising linking sequencing reads obtained from one end of the double-stranded target molecule to sequencing reads obtained from the opposite end of the same double-stranded target molecule.

23. The method of claim 1, wherein the plurality of target nucleic acid molecules comprise a target nucleic acid molecule derived from a circulating tumor cell (CTC), a circulating tumor mitochondrial DNA (ctmtDNA), or a viral DNA.

24. The method of claim 1, wherein a true mutation is a mutation detected in all or substantially all sequencing reads from both strands of the target nucleic acid molecule.

25. The method of claim 1, wherein the target nucleic acid molecules are original double-stranded nucleic acid molecules from a sample of a subject.

* * * * *

SEQUENCE LISTING

```
<160> NUMBER OF SEQ ID NOS: 8

<210> SEQ ID NO 1
<211> LENGTH: 7
<212> TYPE: DNA
<213> ORGANISM: Artificial Sequence
<220> FEATURE:
<223> OTHER INFORMATION: Random cypher sequence
<220> FEATURE:
<221> NAME/KEY: misc_feature
<222> LOCATION: (1)..(7)
<223> OTHER INFORMATION: n = A,T,C or G

<400> SEQUENCE: 1 nnnnnnn                                                              7

<210> SEQ ID NO 2
<211> LENGTH: 195
<212> TYPE: DNA
<213> ORGANISM: Artificial Sequence
<220> FEATURE:
<223> OTHER INFORMATION: An oligonucleotide containing EcoRI and BamHI
      restriction enzyme sites, adapter sequences, indices, and random
      7-nucleotide barcodes flanking a SmaI restriction enzyme site
<220> FEATURE:
<221> NAME/KEY: misc_feature
<222> LOCATION: (1)..(195)
<223> OTHER INFORMATION: n = A,T,C or G

<400> SEQUENCE: 2
```

```
gatacaggat ccaatgatac ggcgaccacc gagatctaca ctagatcgcg cctccctcgc    60
gccatcagag atgtgtataa gagacagnnn nnnncccggg nnnnnnnctg tctcttatac   120
acatctctga gcgggctggc aaggcagacc gtaaggcgaa tctcgtatgc cgtcttctgc   180
ttggaattcg ataca                                                    195

<210> SEQ ID NO 3
<211> LENGTH: 22
<212> TYPE: DNA
<213> ORGANISM: Artificial Sequence
<220> FEATURE:
<223> OTHER INFORMATION: forward primer sequence

<400> SEQUENCE: 3
gatacaggat ccaatgatac gg                                             22

<210> SEQ ID NO 4
<211> LENGTH: 22
<212> TYPE: DNA
<213> ORGANISM: Artificial Sequence
<220> FEATURE:
<223> OTHER INFORMATION: reverse primer sequence

<400> SEQUENCE: 4
tgtatcgaat tccaagcaga ag                                             22

<210> SEQ ID NO 5
<211> LENGTH: 23
<212> TYPE: DNA
<213> ORGANISM: Artificial Sequence
<220> FEATURE:
<223> OTHER INFORMATION: forward primer sequence

<400> SEQUENCE: 5
tctgtctcct tcctcttcct aca                                            23

<210> SEQ ID NO 6
<211> LENGTH: 19
<212> TYPE: DNA
<213> ORGANISM: Artificial Sequence
<220> FEATURE:
<223> OTHER INFORMATION: reverse primer sequence

<400> SEQUENCE: 6
aaccagccct gtcgtctct                                                 19

<210> SEQ ID NO 7
<211> LENGTH: 20
<212> TYPE: DNA
<213> ORGANISM: Artificial Sequence
<220> FEATURE:
<223> OTHER INFORMATION: forward primer sequence

<400> SEQUENCE: 7
aatgatacgg cgaccaccga                                                20

<210> SEQ ID NO 8
<211> LENGTH: 21
<212> TYPE: DNA
<213> ORGANISM: Artificial Sequence
<220> FEATURE:
<223> OTHER INFORMATION: reverse primer sequence
```

```
<400> SEQUENCE: 8
caagcagaag acggcatacg a                                              21
```